(12) United States Patent
Kwon (10) Patent No.: US 8,336,373 B2
(45) Date of Patent: Dec. 25, 2012

(54) MASS SENSING DEVICE FOR LIQUID ENVIRONMENT

(75) Inventor: Jae Wan Kwon, Columbia, MO (US)

(73) Assignee: Curators of the University of Missouri, Columbia, MO (US)

( * ) Notice: Subject to any disclaimer, the term of this patent is extended or adjusted under 35 U.S.C. 154(b) by 435 days.

(21) Appl. No.: 12/755,993

(22) Filed: Apr. 7, 2010

(65) Prior Publication Data

US 2010/0282005 A1 Nov. 11, 2010

Related U.S. Application Data

(60) Provisional application No. 61/212,099, filed on Apr. 7, 2009.

(51) Int. Cl.
*G01N 29/036* (2006.01)

(52) U.S. Cl. .......................... 73/61.79; 73/61.49; 73/865

(58) Field of Classification Search .................... 73/865, 73/31.06, 61.45, 61.49, 61.79
See application file for complete search history.

(56) References Cited

U.S. PATENT DOCUMENTS

| | | | | |
|---|---|---|---|---|
| 6,016,025 | A * | 1/2000 | Wold et al. | 310/369 |
| 2005/0148065 | A1* | 7/2005 | Zhang et al. | 435/287.2 |
| 2006/0197411 | A1* | 9/2006 | Hoen et al. | 310/320 |
| 2011/0285794 | A1* | 11/2011 | Jilani et al. | 347/71 |

* cited by examiner

*Primary Examiner* — Hezron E Williams
*Assistant Examiner* — Paul West
(74) *Attorney, Agent, or Firm* — Polster, Lieder, Woodruff & Lucchesi, L.C.

(57) ABSTRACT

A device for sensing a mass in a liquid environment including a resonator comprising a piezo layer having a top electrode and a bottom electrode, a sensing surface located adjacent and opposite the top electrode, the resonator and the sensing surface defining a gap therebetween, and a post attached to the sensing surface and the resonator.

13 Claims, 9 Drawing Sheets

MASS SENSING DEVICE FOR LIQUID ENVIRONMENT

The present application claims priority to U.S. Provisional Patent Application No. 61/212,099 filed Apr. 7, 2009, the contents of said application are incorporated herein by reference.

FIELD OF THE INVENTION

This invention relates to a mass sensing device for sensing the mass of a substance within a liquid medium.

BACKGROUND OF THE INVENTION

With rapid advancements in semiconductor manufacturing techniques, new classes of miniaturized devices and systems called Microelectromechanical Systems (MEMS) have become prominent. Various MEMS devices and systems utilize tiny (micron level) mechanical and electronic components together in many applications of sensors and actuators. Microfabrication technologies have been well developed for decades due to the growth of integrated circuit manufacturing technologies. One of the first MEMS devices was developed in the mid-1960s using the existing micro fabrication technologies. During the 1980s, many MEMS devices were successfully commercialized. The miniaturized systems have started replacing various conventional sensors in many applications due to the cost effectiveness, small size, low power consumption, high reliability and compatibility with integrated circuits. Any combination of microelectronics, micromechanics, micro-optics, micro-fluidics, and micro-magnetics can be realized on a single substrate using the MEMS technologies.

The most common substrate among many available materials (Table 1) for micromachining is silicon due to its excellent mechanical properties, standardized processing and ease of integrating it with microelectronics. The three major steps for the micromachining of microelectromechanical systems are deposition, lithography and etching.

TABLE 1

Common Materials used in Micromachining

| Materials | Usage | Characteristics |
| --- | --- | --- |
| Polymide | Structure | Soft and flexible, optical guide |
| Tungsten | Structure | Immune to HF attacks |
| Ni, Cu, Au | Structure | Plated thick structures |
| Quartz | Actuation | Piezoelectric |
| ZnO | Actuation | Piezoelectricity |
| PZT | Actuation | Large piezoelectricity |
| TiNi | Actuation | Shape memory alloy |
| GaAs | Optics | Laser, LCD, detector |

There are popular MEMS devices such as pressure sensors, accelerometers, mass sensors, RF switches, optical MEMS devices and microfluidic devices. A few common applications of the MEMS devices include biomedical sensors, drug delivery systems, and various automotive sensors.

In particular, RF-MEMS devices can offer superior performance at high frequencies comparing to many traditional RF devices. For example, MEMS-based RF switches and variable capacitors require lower actuation voltages than the traditional semiconductor based devices. Additionally, many former attempts on RF MEMS phase shifters offering tremendous advantages over GaAs based semiconductor phase shifters have been reported. Furthermore, MEMS devices can even be implanted in human body.

Figure 1:
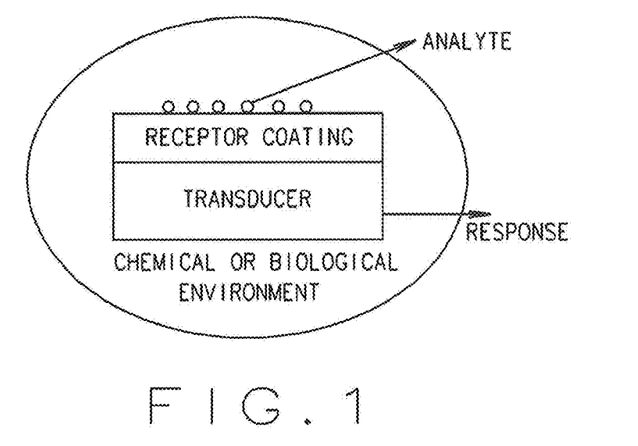
FIG. 1 is a schematic representation of a mass sensor.

Mass sensors are one of the popular MEMS sensors that are commonly used for biological and chemical sensing. Micromachined mass sensors can recognize a change in mass via a change in their oscillating frequencies. A mass sensor's sensing area is generally treated with a binding layer that selectively binds the target chemical or biological analyte as shown in FIG. 1.

Micromachined cantilever is the most popular mass sensor type. It utilizes a single clamped mechanical beam. Cantilever mass sensors are classified as "Static" or "Dynamic" by their mode of operation. In the static mode, there is a mechanical movement or deformation of the beam as the surface stress varies, which is induced by the adsorption of atoms on atomically pure surfaces. Chemically induced stress has also been extensively studied. All the stresses can cause a deflection motion in the cantilever beam structure.

In the resonance mode, the MEMS based cantilever can be regarded as a weakly damped oscillator in the presence of gases or under vacuum. The resonance can be observed by transducing the mechanical resonance into an excitation in the electric field, acoustic field or electromagnetic field. The resonant frequency is affected by mass loading, mechanical damping or a spring constant. By observing the change of the resonant frequency, a variation of the mass can be detected.

Cantilever mass sensor systems use the change in cantilever parameters like cantilever tip position, radius of curvature, intrinsic stress or resonance frequency to detect mass. The mass sensors employ various readout schemes, including optical, piezoresistive, and piezoelectric methods. There are inherent advantages and disadvantages for each readout scheme and an optimum readout scheme has to be chosen depending on the application.

Micromachined mass sensors based on acoustic resonators have many advantages, including low cost of manufacturing and high sensitivity. Acoustic mass sensors are based on the fact that the resonant frequency changes with a change of the mass on the resonator surface. There are two popular types of acoustic mass sensors which are in common use: surface acoustic wave devices and bulk acoustic wave devices.

Surface acoustic wave devices (SAW) utilize surface waves that have particle displacement in directions both perpendicular and parallel to the wave's propagation and have been used as a highly sensitive mass detector. SAW devices use two interdigital transducers (IDTs) with a sensing area in between. One of the IDT is called the input IDT and generates acoustic waves. The other IDT is called the output IDT and converts the acoustic waves into the electric signals. The surface acoustic waves produced by an RF signal travel along the delay path caused by the added mass.

Figure 2:
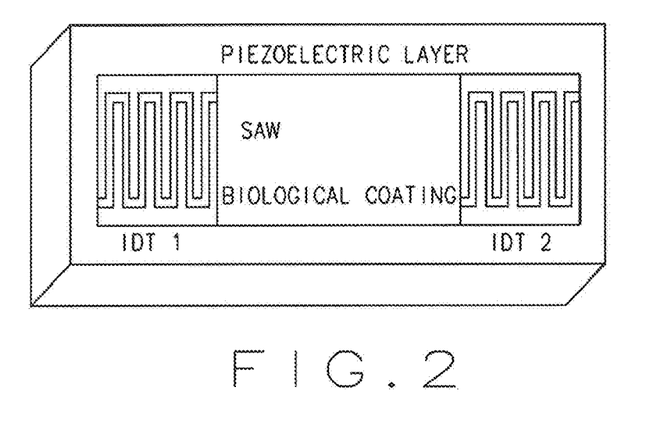
FIG. 2 is a schematic of a SAW mass sensor with a biologic coating.

The fabrication of SAW sensors is simple and the typical Quality factor (Q) value is in the range of 10,000. Generally, SAW devices are coated with a thin film (FIG. 2) that can selectively interact with a chemical or biological analyte. The added mass that is absorbed by the sensing film causes a change in the velocity or an attenuation of the amplitude of the SAW. This change in parameters of the SAW provides the sensing mechanism.

Bulk Acoustic Wave (BAW) devices utilize longitudinal or shear acoustic waves which propagate through the bulk of the substrate unlike a SAW. Quartz Crystal Microbalance (QCM) and Film Bulk Acoustic Resonator (FBAR) are the two popular BAW devices.

A QCM consists of a thin quartz substrate and two electrodes plated on both side. When an alternating electric field is applied across the quartz crystal, acoustic waves are produced in the crystal. Resonance condition occurs when the thickness of the quartz disk is a multiple of one half wavelength of the acoustic wave. In the QCM, the acoustic wave propagation is in a direction perpendicular to the crystal surface. The resonant frequency depends on the thickness, shape and mass of the quartz. Thus any change of mass results in a change in resonance frequency. It can be safely assumed that the change in frequency is directly proportional to the amount of mass deposited on the QCM.

$$\Delta f \propto K \Delta m$$

However, the higher range of the quartz's resonance frequency is technically limited by the thickness of the quartz disk since it is not easy to reduce the thickness of the quartz. On the other hands, Film Bulk Acoustic Resonator (FBAR) is also a BAW sensor but uses a very thin piezoelectric film. As the piezoelectric layer thickness can be reduced down to a few hundreds of nanometers, a high resonance frequency can be attained in the range of GHz.

An FBAR device consists of a thin piezoelectric film that is sandwiched between two electrodes. When an alternating electric field is applied to the piezoelectric layer, acoustic waves are produced. The acoustic waves form a standing wave pattern if the frequency of the applied electric filed matches the fundamental resonant frequency of the device. The fundamental resonant frequency is inversely proportional to the thickness of the piezoelectric film.

FBAR has many advantages over the QCM. Since the FBARs have a thin film piezoelectric layer as the active layer, very high resonance frequencies can be obtained. The fabrication of an FBAR is compatible with standard integrated circuit (IC) process. The lateral dimensions can be equal to the thickness dimensions resulting in very small FBAR sensors. The sensitivity of the FBAR mass sensors was shown to be about 50 times better than that of typical QCM sensors.

SUMMARY OF THE INVENTION

The present invention comprises a device for sensing a mass in a liquid environment. The device comprises a resonator comprising a piezo layer having a top electrode and a bottom electrode, a sensing surface located adjacent and above the top electrode, the resonator and the sensing surface defining a gap therebetween, and posts attached to the sensing surface and the resonator.

DESCRIPTION OF THE DRAWINGS

FIGS. 11a-l illustrate fabrication steps of the preferred embodiment of the present invention;

DETAILED DESCRIPTION OF THE PREFERRED EMBODIMENT

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Figure 3:
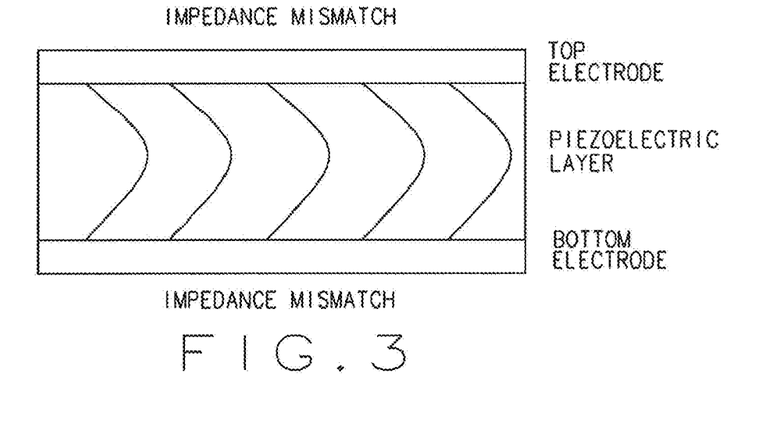
FIG. 3 is a FBAR device showing standing wave pattern.

A micromachined Film Bulk Acoustic Resonator (FBAR) converts electrical energy to mechanical energy or vice versa. The basic structure of an FBAR consists of a piezoelectric thin film and a pair of electrodes on both surfaces (FIG. 3). The FBAR can be classified as thickness field excitation (TFE) and lateral field excitation (LFE) FBARs depending on the direction of the excitation field (electric field). The excitation field is perpendicular to the surface in the TFE FBARs, while the excitation field is parallel with the surface in the LFE FBARs as well-illustrated in FIGS. 4a and 4b.

Figure 4A:
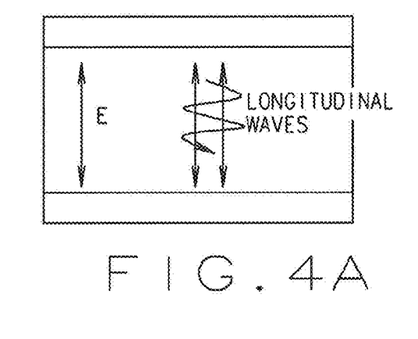
FIGS. 4a and 4b illustrate a thickness field excitation FBAR and a lateral field excitation FBAR, respectively.
Figure 4B:
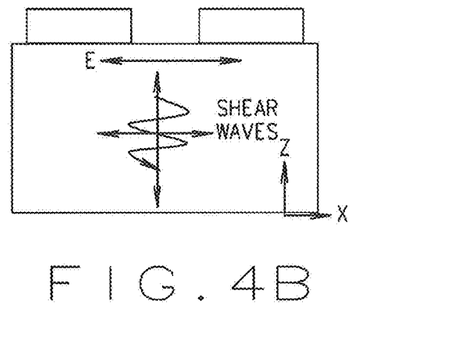
Figure 5A:
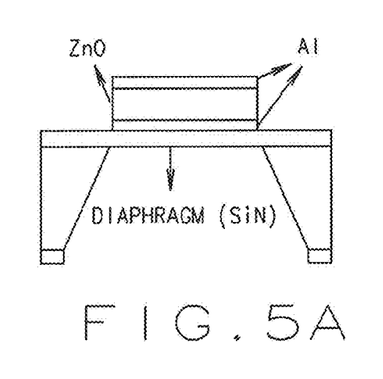
FIGS. 5a and 5b illustrate an air backed FBAR and a Bragg reflector FBAR, respectively.
Figure 5B:
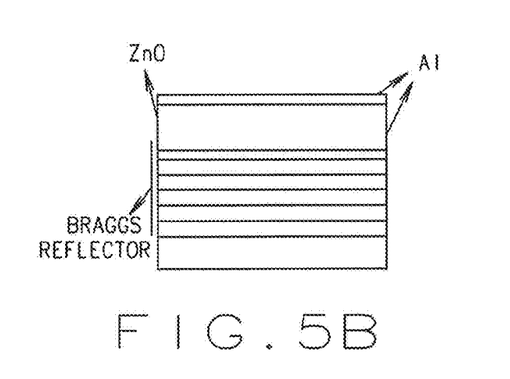

A TFE FBAR generates a z-propagating longitudinal wave when an alternating electric field is applied in the z-direction. Most of the waves are reflected back at the top and bottom surfaces of the device due to acoustic impedance mismatch and a standing wave is formed at the resonance, where the excitation signal frequency is equal to $V_a/2d$ where $V_a$ and $d$ are the acoustic-wave velocity and piezoelectric film thickness, respectively. The acoustic standing wave modifies the electric field distribution inside the piezoelectric film, which changes the electrical impedance of the device. Thus, the electrical impedance of the resonator varies with frequency. As shown in FIG. 4a, the top and bottom surface of the FBAR is surrounded by air, which can act as a good reflector of the acoustic waves and help keep the acoustic energy within the piezoelectric material. In the LFE FBAR as shown in FIG. 4b, the excitation field is along the surface and produce shear acoustic waves in the Z direction when the electric field is applied in the X or Y direction. This shear wave propagates along the thickness of the film. In a TFE FBAR, the electrodes occupy a larger portion of the FBAR at higher frequencies, thereby reducing the Q factor. But the LFE FBAR structure eliminates one electrode layer and hence has a higher Q than TFE FBAR The acoustic waves produced by the alternating electric field travel through the bulk of the device. The reflection of the acoustic wave can happen by having the FBAR structure on a diaphragm as shown in FIG. 5(a). However, the drawback of the diaphragm approach is the weakened sustainability to the stress on the films. The diaphragm structure is too fragile and is easily broken. They also have limited power handling capacity. Another way to achieve the reflection of the acoustic wave is to use Bragg reflectors as shown in FIG. 5(b). The Bragg reflector consists of alternating stacks of quarter wavelength layers of low and high acoustic impedance. The acoustic wave is reflected at each layer of the reflector. Silicon dioxide is the typical material used for the low impedance layer and tungsten, molybdenum or aluminum nitride is used for the high impedance layers. However there is a Q factor limitation due to the increased mass loading of the reflector layers.

When the thickness of the thin film is equal to an integer multiple of one half of the wavelength, the resonance condition occurs due to the formation of a standing wave. The fundamental resonance frequency is inversely proportional to the thickness of the piezoelectric material used. The fundamental resonant frequency is given by f=v/2d, where v is the acoustic velocity in the piezoelectric material and d is the thickness of the piezoelectric material. For zinc oxide, which is one of the most popular piezoelectric materials used for FBARs, the relation between the stress and the electric field is given by the equation below.

$$\begin{bmatrix} 0 & 0 & e_{31} \\ 0 & 0 & e_{31} \\ 0 & 0 & e_{33} \\ 0 & e_{15} & 0 \\ e_{15} & 0 & 0 \\ 0 & 0 & 0 \end{bmatrix} \begin{bmatrix} E_x \\ E_y \\ E_z \end{bmatrix} = \begin{bmatrix} T_1 \\ T_2 \\ T_3 \\ T_4 \\ T_5 \\ 0 \end{bmatrix}$$

A z-directed elastic wave in a solid propagates in the z-direction. The molecules vibrate in the z-direction to produce a stress $T_3$ for a longitudinal wave. For a shear wave, they vibrate in y-direction to produce stress $T_4$ or in x-direction to produce stress $T_5$. For a piezoelectric material, these mechanical variables (stress T or strain S) are coupled with electrical variables (electric field E or electric displacement D. From the above equation, $T_1=e_{31}E_z$, $T_2=e_{31}E_z$, $T_3=e_{33}E_z$, $T_4=e_{15}E_y$, and $T_5=e_{15}E_x$. Thus, a z-directed external electric field produces a z-propagating longitudinal acoustic wave (LW) and x or y directed electric field produces z-propagating shear acoustic wave (SW).

Figure 6:
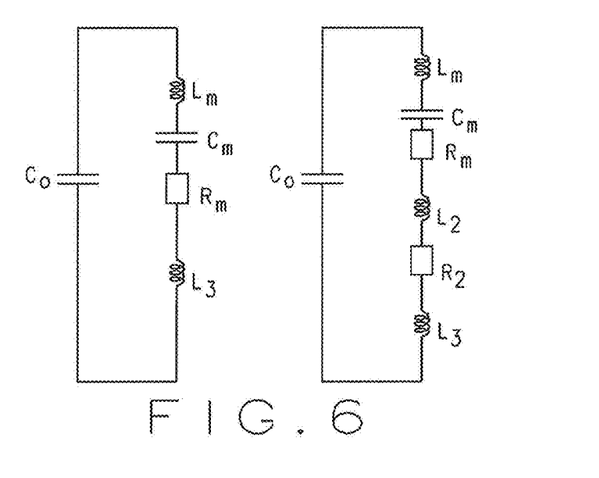
FIG. 6 is a comparison of schematics showing a Butterworth-Van Dyke model of an FBAR with mass loading in air on the left and a mass loading in liquid on the right.

An FBAR can be modeled electrically by the Butterworth-Van Dyke (BVD) equivalent circuit as shown in FIG. 6. The resonator is modeled by a constant "clamped" capacitance $C_o$ in parallel with an acoustic or "motional" arm that consists of motional capacitance $C_m$, motional inductance $L_m$, and motional resistance $R_m$ in series. The $C_o$ models the electrical capacitance between the two electrodes through which the electric field is applied. The motional components ($C_m$, $L_m$ and $R_m$) model electromechanical response of a piezoelectric material. The component $L_m$ is called motional inductance and $R_m$ is called motional resistance. Assuming $R_m=0$ and neglecting $L_2$ which is due to mass loading we can write the impedance of the BVD circuit (FIG. 6) as:

$$X(S) = \frac{1 + L_m C_m S^2}{S(S^2 L_m C_m C_o + C_m + C_o)}$$

with S=jω, the series resonant frequency ($\omega_s$) and the parallel resonant frequency ($\omega_p$) are obtained by setting X(jω$_s$)=0 and X(jω$_p$)=∝, respectively.

$$\omega_s^2 = \frac{1}{L_m C_m} \text{ and } \omega_p^2 = \omega_s^2 \left[ 1 + \frac{C_m}{C_o} \right]$$

From the above equations, ratio of $C_m$ and $C_o$ is obtained to be $$C_r = \frac{C_m}{C_o} = \frac{f_p^2 - f_s^2}{f_s^2} \approx 2\frac{(f_p - f_s)}{f_s}$$

$C_r$ is related to the electromechanical coupling constant as $$C_r = \frac{8K_{eff}^2}{\pi^2 N^2}$$

where $K_{eff}^2$ and N are the effective electromechanical coupling constant of the piezoelectric layer and the number of acoustic half wavelengths in the piezoelectric layer respectively. Thus, the higher the capacitance ratio $C_r$ (or the larger the electromechanical coupling coefficient $K_{eff}^2$), the wider the bandwidth $\Delta f = f_p - f_s$.

In the case of FBAR, $R_m$ represents the energy loss in the piezoelectric layer, the supporting layer and the metal electrode layers and air damping, which limits the Q of a FBAR. When the FBAR is loaded with mass or when the FBAR is in liquid with mass loading, the BVD equivalent circuit is as shown in the FIG. 6. In FIG. 6, the BVD circuit represents the case of mass loading only in air. The extra component in the circuit is $L_3$, which is caused by the extra mass.

It is inferred that mass loading causes the impedance to be predominantly inductive. $L_3$ represents the mass loading effect and causes reduction at the resonant frequency. $L_2$ represent mass loading effect due to mass respectively and $R_2$ is associated with the energy loss due to the liquid. The components $L_m$, $R_m$ and $L_3$ are related to the added mass through the following equations:

$$L_m = \frac{1}{4\pi^2 f_s^2 C_m}$$

$$R_m = \frac{\eta_0}{\theta_0^2 \rho_0 C_m} \left( \frac{f}{f_s} \right)$$

$$L_2 = \frac{4 f_s \rho_3 L_m d_3}{\rho_0 v_0}$$

Where
  A is the area of the resonator
  $d_0$ is the thickness of the piezoelectric layer
  ε is the permittivity of the piezoelectric layer
  $K^2_t$ is the electromechanical coupling constant
  $\eta_0$ is the acoustic velocity in the piezoelectric layer
  $\rho_0$ is the density of the piezoelectric layer
  $\rho_3$ is the density of added mass
  $\theta_0$ is the acoustic velocity in the piezoelectric layer
  $d_3$ is the thickness of the added mass In the case of liquid loading, the mass loading due to the liquid ($L_2$) is negligible but the loss ($R_2$) is very big and much greater than $R_m$. The Q factor of the FBAR with mass loading in liquid is given by $$Q = \frac{\omega L}{R} = \frac{2\pi(L_m + L_2 + L_3)}{R_m + R_2}$$

As $R_2 \gg R_m$, Q drops drastically in the presence of liquid. From the above equations, the frequency shift due to additional mass loading is $$\frac{\Delta f_s}{f_s} \approx -\frac{\rho_3 d_3}{\rho_0 d_0}$$

The above equations describe a linear relationship between the change of frequency and additional mass. But the linearity is valid only when the added mass does not exceed 2% of the resonator mass because the elastic modulus of the added mass layer also affects the resonant frequency as the mass loading gets larger.

Former studies reported a significant drop of Q factor from 200 to about 10 in water for the fundamental frequency of resonance. The reduction of Q factor affects the minimum detectable mass due to increased noise in the magnitude and phase plot.

Figure 7A:
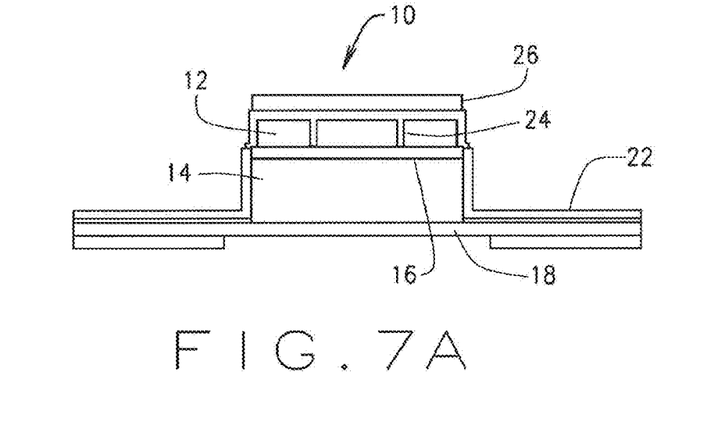
FIGS. 7a and 7b are a side view and a perspective view, respectively, of a device according to an embodiment of the present invention.
Figure 7B:
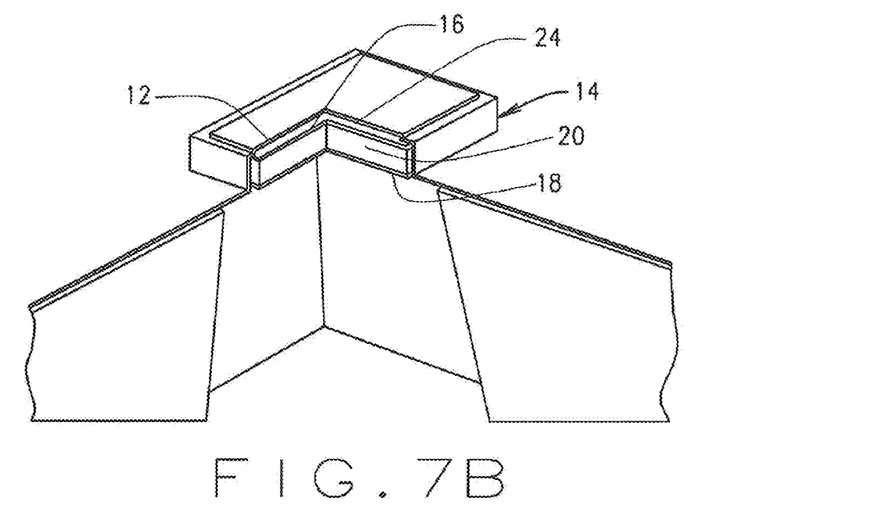

There are many factors that cause a reduction of Q factor in the liquid medium. For a high Q factor, the acoustic energy in an FBAR has to be well trapped within the piezoelectric layer. But the longitudinal acoustic-wave energy leaks into the liquid and is lost there since liquid drastically attenuates high-frequency acoustic waves when a liquid is in direct contact with any surface of an FBAR. Attempts have been made to improve the Q factor of FBARs in liquids. The second harmonic resonance of the FBAR was shown to have a Q factor several times higher than the fundamental resonance in a liquid medium. In contrast to the longitudinal acoustic waves, shear acoustic waves do not produce any compressional motion in the liquid, thus avoiding the acoustic energy leakage. The Q factor of the shear acoustic wave device with 50% reduction of Q in water has also been reported. To achieve low loss in liquid environments, longitudinal acoustic wave devices need to be used and the leakage of the acoustic waves into the liquid has to be minimized In that regard, the preferred embodiment of the present invention is a novel design of a film bulk acoustic resonator (FBAR) that has high Q in liquid environments. The new design utilizes a thin gap as an acoustic energy loss isolation layer of the resonator in the liquid. As shown in FIG. 7, the device 10 comprises a gap 12 located between a resonator 14 comprising a top electrode 16, a bottom electrode 18 and a piezo layer 20. The gap 12 is preferable a vacuum gap but may also comprise an air gap. The resonator 14 is preferably an FBAR, but may comprise any SAW or BAW.

The vacuum or air gap 12 reduces the direct contact area at the interface between FBAR and liquid. The vacuum separation is achieved by using a parylene diaphragm 22 supported by micro-posts 24. A sensing surface 26 comprising a sensing coating is located above the vacuum or air gap 12 attracts and bonds with a mass to be measured. The significant energy loss caused by the liquid damping can be remarkably reduced with this design. A small fraction of longitudinal waves can leak to the liquid medium through the micro-posts 24 and get attenuated drastically. However, most of the acoustic waves are reflected back into the device at the interface between the resonator 14 and the vacuum or air gap 12 due to the large acoustic impedance mismatch. Thus, most of the acoustic energy turns out to be trapped within the piezoelectric layer 20. In addition, the vacuum gap 12 prevents the squeeze film damping effect, which comes into play when any gas is trapped between two vibrating surfaces close to each other. Although an air or gas gap 12 suffers this detriment, it will still perform acceptably in most applications. When a liquid material is loaded onto the top parylene diaphragm 22, the mass can be transferred onto the active FBAR area by adherence to the sensing coating 26 through the micro-posts 24. This causes a shift in the resonant frequency proportional to the mass loaded onto the FBAR and thus the mass may be measured with the device 10. The Q factor and the sensitivity of FBAR are affected by the materials used for the piezoelectric layer, electrodes and diaphragm.

Before depositing the parylene diaphragm layer 22, a thin low stress LPCVD Silicon Nitride ($Si_xN_y$) film should exist as the supporting diaphragm for the device. The thickness of the diaphragm is 0.8 microns. The silicon nitride acts as an excellent etch mask while using bulk-micromachining to make the diaphragm. If the $Si_xN_y$ layer is too thin, the device is fragile and the supporting diaphragm is easily broken. A thickness of 0.8 microns is used because a thinner diaphragm is too fragile and a thicker diaphragm can reduce the mass sensitivity of the sensor.

Aluminum is used as the bottom electrode 18. The thickness of the electrode 18 is 1000 angstroms. Aluminum has low resistivity ($2.82 \times 10^{-8}$ Ω-m at 20° C.) which reduces the electrical losses. It has a low mass density (2.702 g/cm$^3$) to minimize the mass loading effect. It compares favorably with other common electrodes like platinum (21.45 g/cm$^3$) and tungsten (19.3 g/cm$^3$).

An aluminum layer of 0.1 micron thickness is used for the electrodes. A thicker layer of the metal would decrease the resistive loses but it would also increase the mass loading on the FBAR, thereby reducing the resonant frequency and mass sensitivity. Aluminum has an acoustic velocity of 6420 m/s and an acoustic impedance of $17.3 \times 10^6$ kg/m$^2$ s.

Figure 8:
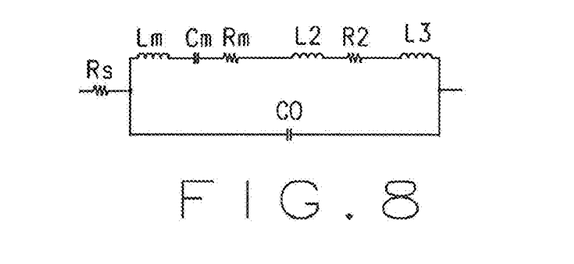
FIG. 8 is a schematic of a Butterworth-Van Dyke equivalent circuit for an FBAR in liquid.

The piezoelectric layer 20 is zinc oxide (ZnO) and is an active piezoelectric layer. The choice of piezoelectric layer is the most crucial factor that affects the properties such as Q factor, sensitivity and resonant frequency. The resonant frequency of a ZnO based FBAR can be approximated by the following equation:

$$f_r = \frac{1}{2t}\sqrt{\left(\frac{c^E_{33}}{\rho}\right)}\left(\frac{1 - 0.41k_t^2}{1 - 0.5k_t^2}\right)$$

where $\rho$, $t$, $c^E_{33}$, $K_t$ are the density, thickness, stiffness coefficient and piezoelectric coupling coefficient of the ZnO thin film. ZnO has a higher piezoelectric coupling coefficient (8.5%) than that of aluminum nitride (6.5%);

The FBAR can be modeled using a Butterworth Van Dyke (BVD) model as described above. The model is shown in FIG. 8:

The model of FIG. 8 includes the effect of mass loading in liquid environments. When the FBAR operates in a liquid environment, the Q factor decreases greatly due to a very high acoustic viscosity in the liquid compared to that in a solid. Higher viscosity means more energy loss of the acoustic wave as it propagates in the liquid. The term $R_2$ in the model is due to the loss in liquid due to the leakage of longitudinal waves into the liquid medium. The loss due to mass loading is negligible.

The Q factor is given by the following equation:

$$Q = \frac{\omega L}{R} = \frac{2\pi f_s (L_m + L_2 + L_3)}{R_m + R_2}$$

The term $R_m + R_2$ is the lossy component in the model. The loss due to the liquid $R_2$ is much greater than $R_m$ and Q factor can be improved by reducing the value of $R_2$. In the preferred embodiment, because the leakage of the acoustic wave is negligible due to the vacuum layer, the $R_2$ parameter can be neglected.

The acoustic energy leakage depends on the total percentage of the micro post area. In the preferred embodiment, micro posts with a thickness of less than 10 micron cover about 5 to 8% of total active area. Considering the worst case scenario of the largest coverage area (8%), we can assume that a total of 8% of the longitudinal waves are directly contact with the liquid layer and 8% of total energy can theoretically be absorbed by the liquid since there is some reflection of the waves at the liquid interface. The acoustic impedance of aluminum (top electrode) is 17.3 Megarayls and that of parylene is 2.8 Megarayls. The reflection coefficient is given by:

$$R = ((Z_1 - Z_2)/(Z_2 + Z_1))^2$$

where $Z_2 = 2.8$ and $Z_1 = 17.3$. Therefore $R = 0.5256$. The transmission coefficient is $1 - 0.5256 = 0.4744$ Considering the worst case scenario of the entire transmitted wave being absorbed by the liquid, the leaked energy turns out to be about (8 times 0.4744) % = 3.7952%.

A Finite Element Analysis (FEA) software tool, COVENTORWARE was used to simulate the new design with a vacuum layer (acoustic loss isolation layer) formed by micropost structures. The following three cases have been simulated since the position and the number of the micro-posts is very important criteria in designing the acoustic loss isolation layer in a liquid environment. The first case is when there is no supporting micro-post under the surrounding clamped boundary condition. The second case is when there is one supporting micro-post in the middle of the layer. The third case is when there are four supporting micro-posts.

When the FBAR oscillates, it affects the oscillations of the sensing diaphragm through the posts. However, this is negligible since the resonant frequency of the FBAR matches with neither the fundamental mode of the sensing diaphragm nor with any of its dominant harmonics. Even if the resonance frequency of the FBAR matches with the very high harmonics of the sensing diaphragm, it won't affect the FBAR's Q factor much because the very high harmonics oscillations are well damped.

Figure 9:
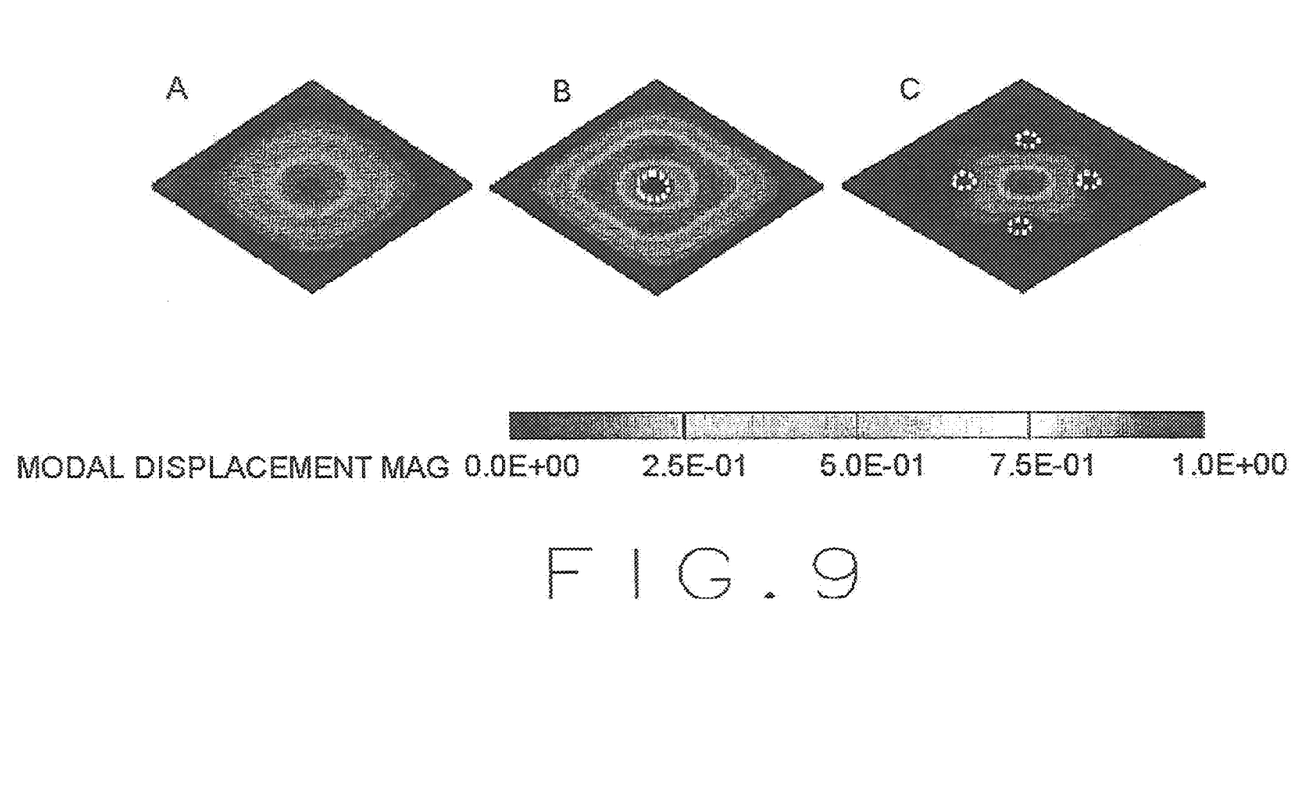
FIG. 9 is a diagram of a modal displacement analysis at fundamental resonant frequencies of the preferred embodiment of the present invention at frequencies of (a) 10.4881 kHz (b) 24.982748 kHz (c) 33.0402 kHz.

To find the resonant frequencies and modal displacements of the sensing diaphragm, the resonant frequency and modal displacement of the sensing diaphragm with different numbers of micro-posts is simulated (FIG. 9)

From FIG. 9, the modal displacement is smallest in the third case (with 4 supporting micro-posts). Less modal displacement means that there is less energy loss by damping into the liquid media while it is oscillating in a liquid environment. It can be seen from FIG. 9 that not only the number but also the location of the micro-posts affects the modal displacement.

Increasing the number of the micro-posts reduces the modal displacement but increases the stability of the sensing diaphragm. On the other hand, as the number of the micro-posts increases, acoustic energy loss through the micro-posts to the liquid increases. Hence, the optimum number of micro-posts should be chosen to meet following criteria: 1. They should support the diaphragm structure well over the thin vacuum or air gap and 2. They should minimize the acoustic energy leakage.

Performing harmonic analysis, in addition to the three cases above (the behavior of the parylene diaphragm as the number of micro-posts is changed), we have also performed simulations of the structure in a liquid environment when it is excited at a signal of 1 GHz, the resonant frequency of the sample FBAR. In the actual device, the parylene diaphragm is connected to the FBAR through the micro-posts. When the FBAR is excited and oscillates at its resonance frequency (1 GHz), the sensing diaphragm is excited as well but not affected by the FBAR's resonance since it has a different resonant frequency as shown in FIG. 10.

Figure 10:
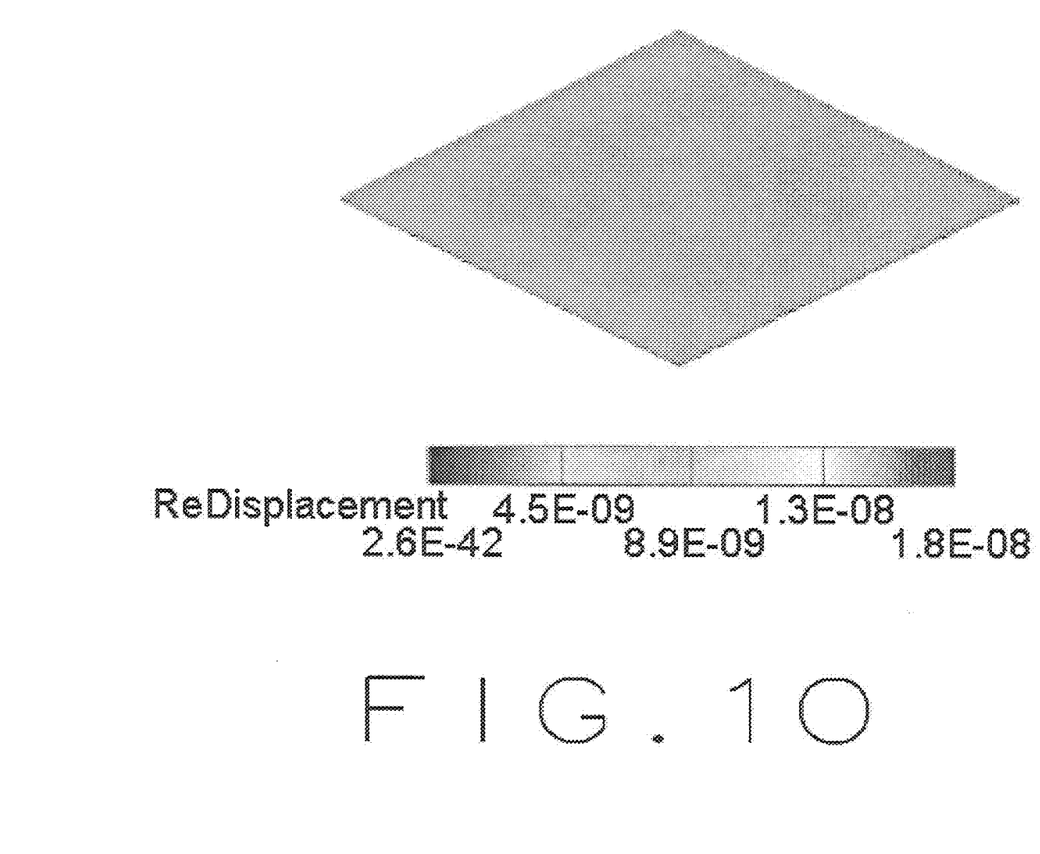
FIG. 10 is a harmonic analysis of the preferred embodiment of the present invention when excited at a frequency of 1 GHz.

FIG. 10 shows the response of the parylene diaphragm without micro-posts. It is supported only by the clamped boundary. Comparing this picture to the resonance picture in FIG. 9(a) in the first case described above (for a zero-post structure), we can see that the modal displacement is much less than the displacement during resonance.

Figure 11:
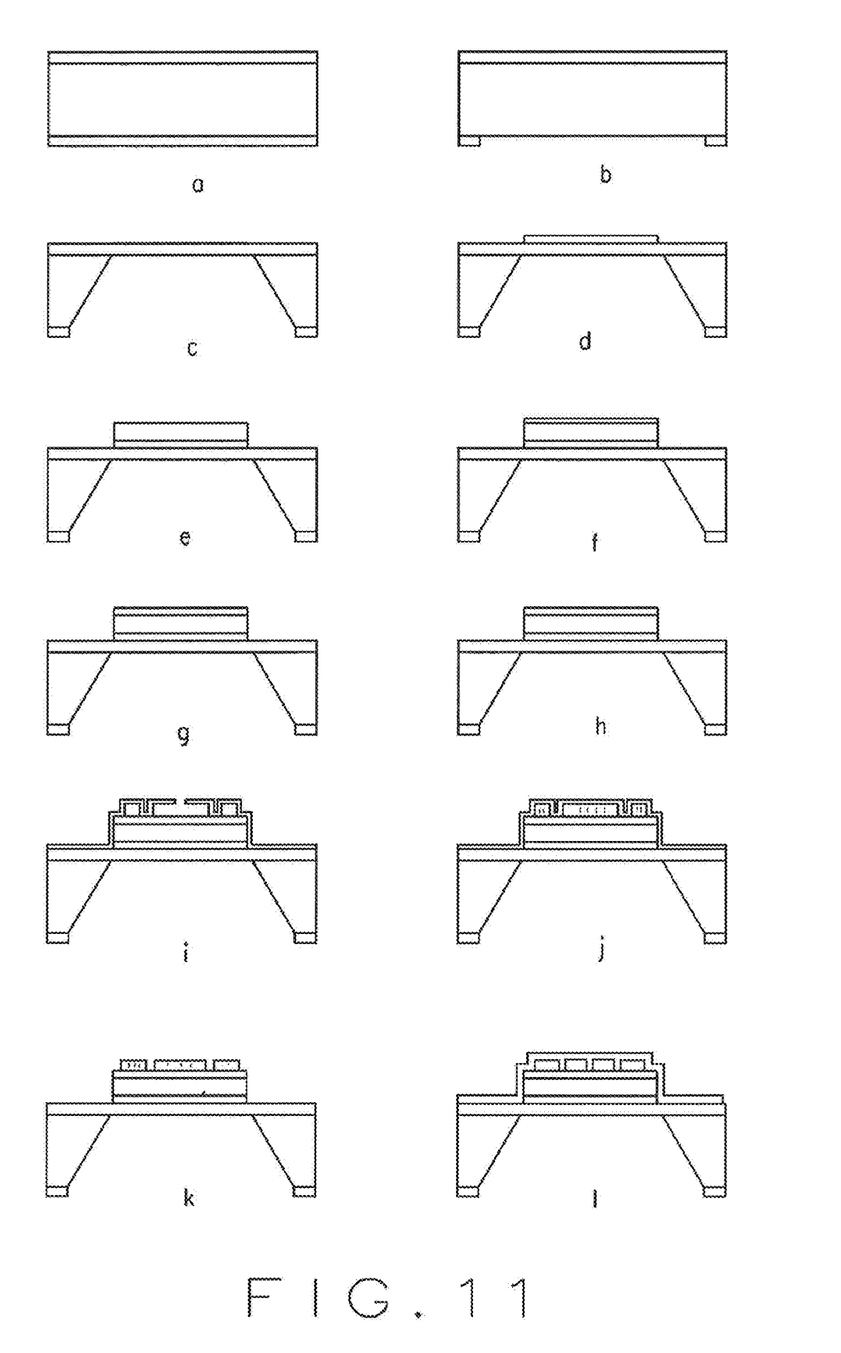

Bulk micromachining and surface micromachining techniques have been used to fabricate the device. FIG. 11 shows in detail fabrication steps. First, a 0.6 micron Low Pressure Chemical Vapor Deposition (LPCVD) Silicon Nitride ($Si_xN_y$) is deposited on both sides of a 400 μm-thick 3 inch silicon wafer (FIG. 11(a)). Then, the silicon nitride is patterned and etched by using reactive ion etching (RIE) with $CF_4$ gas (FIG. 11(b)). The silicon is then completely etched from the back side using 45% KOH solution to make the supporting diaphragm (FIG. 11(c)). After aluminum is deposited and patterned to make the bottom electrode (FIG. 11(d)), zinc oxide is deposited and patterned on it (FIG. 11(e)). The top aluminum layer is followed by the surface treatment with A174 (adhesion promoter to improve the parylene adhesion) (FIG. 11(f)). Once a thin layer of parylene is coated on the substrate (FIG. 11(g)), the active area of the device is patterned out (FIG. 11(h)). In particular, the parylene layer is treated with oxygen plasma to make the surface rough which enhances the adhesion with the second parylene layer that is needed for the top diaphragm. A coating of photoresist (AZ5214) is used as a sacrificial layer 11(i)). Then, a thick parylene layer (1.6 microns) is deposited to form the top diaphragm 11(j)). An etch hole is made on the parylene layer by RIE and the sacrificial layer is removed by acetone 11(k)). Finally, the etch hole is covered by depositing a parylene layer over it 11(l)).

To test the preferred embodiment, the device was characterized with HP 8753D network analyzer and S11 parameters of the device were measured. The device was probed using an RF probe (150 micron pitch) to measure $S_{11}$ parameters from a network analyzer (HP8453D).

The device was tested under three conditions:
   S11 parameters measured in air environment
   S11 parameters measured with water on the back side of the device
   S11 parameters measured with water on the front side of the device The resonant frequency of the sensor was around 2.85 GHz. The Q factor was measured to be about 153 in the air and 140 in the water. The Q factor was only reduced 9% in water, while the Q factor of a normal FBAR in water is drastically decreased down to about 20, which is a reduction of about 85%.

Figure 12:
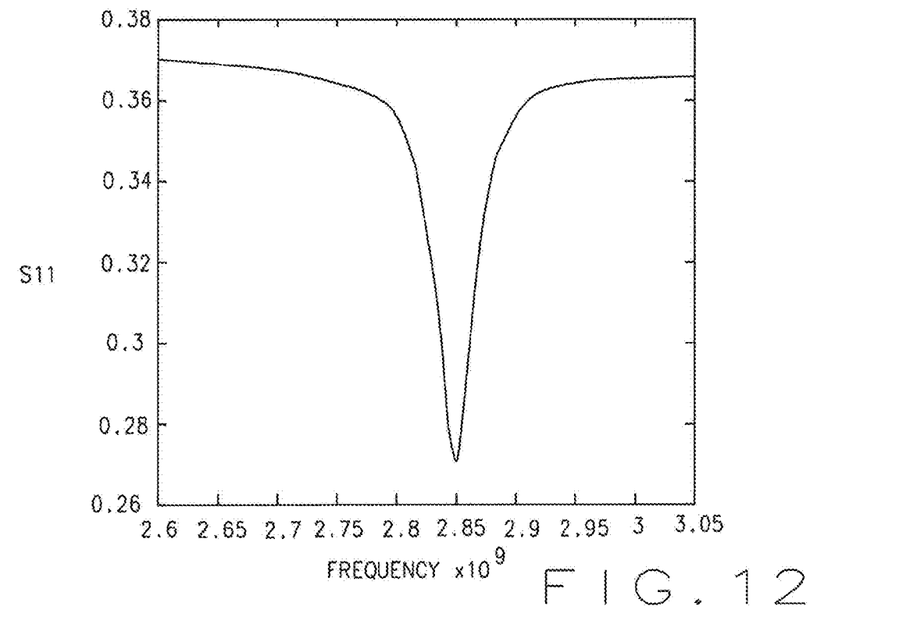
FIG. 12 is a graph of the S11 parameters of the preferred embodiment of the present invention as measured in air.

FIG. 12 shows the S11 parameter plot of the device when in air. The Q factor of the device in air was found to be 153.

Figure 13:
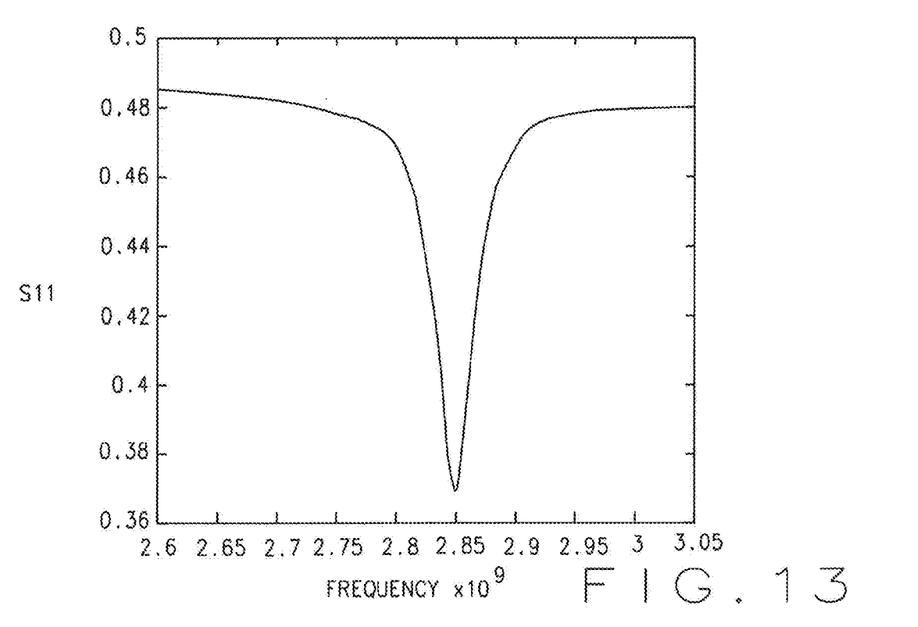
FIG. 13 is a graph of the S11 parameters of the preferred embodiment of the present invention as measured with water on the front side of the device.

FIG. 13 shows the S11 parameter plot of the device with water on the front side with a vacuum gap. The Q factor of the device with water loading on front was found to be about 140.

Figure 14:
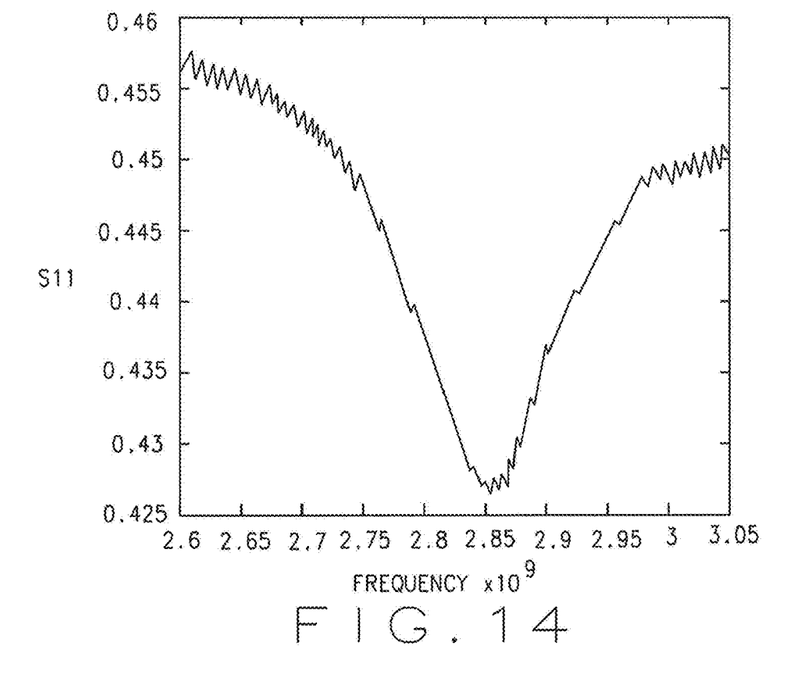
FIG. 14 is a graph of the S11 parameters of the preferred embodiment of the present invention as measured with water on the back side of the device.

FIG. 14 shows the S11 parameter plot of the device with water on the back side where no vacuum/air gap. Thus this may represent the result of conventional FBARs.

The Q factor of the device was found to be about 20

Figure 15:
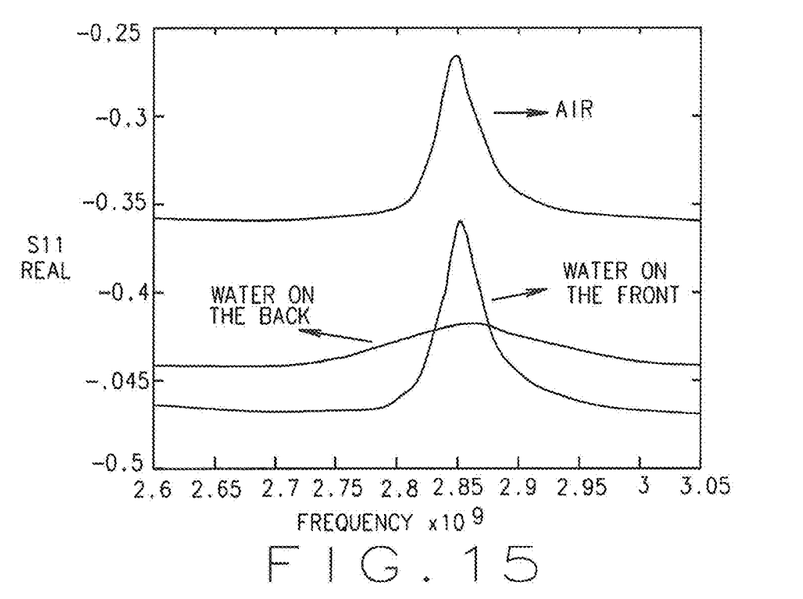
FIG. 15 is a combined graph of the S11 parameters of FIGS. 12-14.
Figure 16:
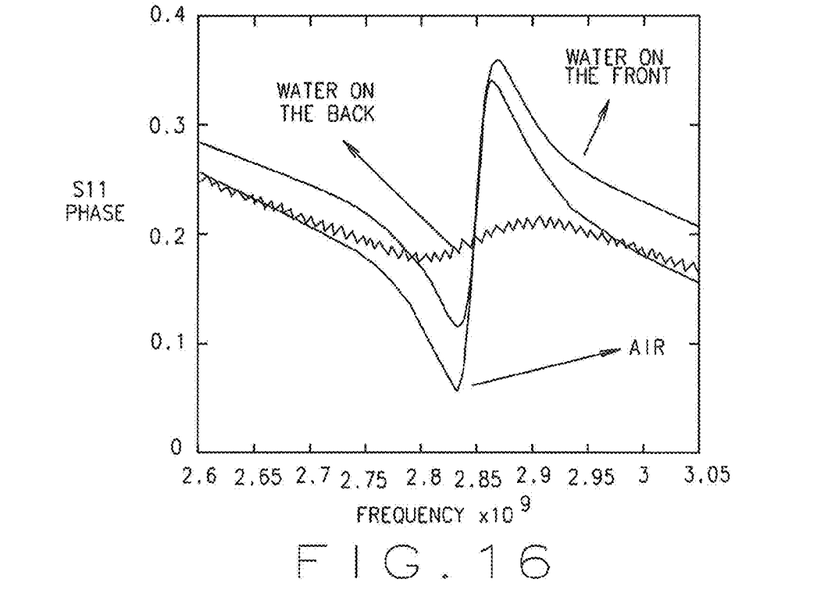
FIG. 16 is a phase plots of the S11 parameters of the preferred embodiment of the present invention is subjected to air, water on the front side of the device and water on the back side of the device.
Figure 17:
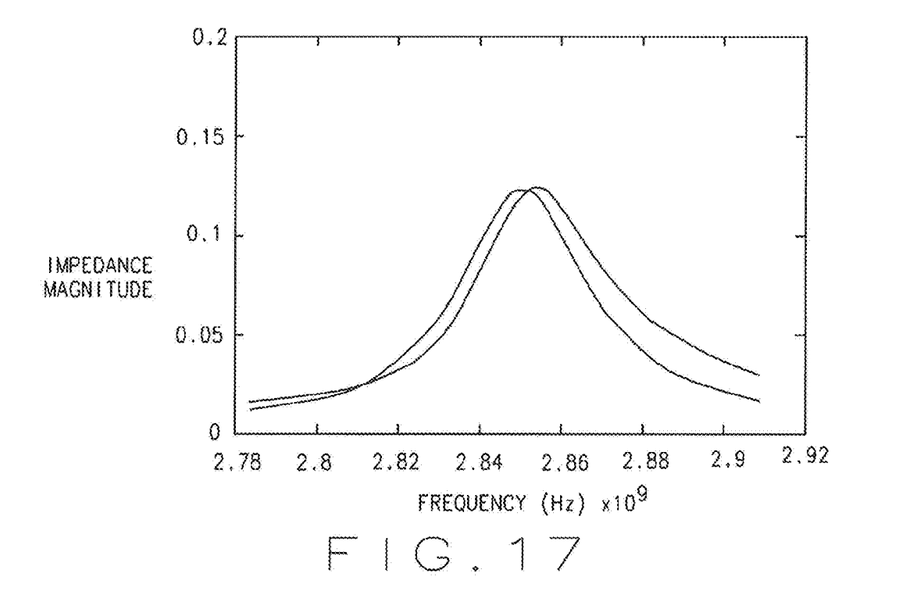
FIG. 17 is a graph of the resonant frequency of a device according to the preferred embodiment of the present invention in water with a 50 nm-thick aluminum film loading.

The response of the sensor in the three cases can be compared in FIG. 15. It can be observed that there is a drastic drop in Q factor when the water is loaded on the back side of the device. This is expected as the liquid is in direct contact with the active area of the device. The vacuum gap provides complete isolation of the active area from the liquid, thereby decreasing energy leakage and increasing the Q factor For the mass sensing in the liquid, a 50 nm thick aluminum ($2 \times 10^{-15}$ g) was deposited on the top parylene surface within the active area. FIG. 17 shows that a resonant frequency shift of 5.4 MHz in the water were observed clearly due to the high Q factor in the liquid by successful separation of liquid damping from the operating frequency of the device.

It is anticipated that the certain approaches will provide additional benefits to the device to reduce energy loss. For example, the performance can also be increased by finding the optimum thickness of the electrode material. Having thicker electrode material results in lower series resistance and hence lower resistive losses. However, thicker electrodes cause the ratio of the inactive-active layer to increase. To achieve a good ratio of the active layer in the device, thin electrodes layers should be used. Alternative electrode materials molybdenum (Mo) and ruthenium (Ru) can give better boundary conditions, low acoustic attenuation, high electrical conductivity, low density and process compatibility with AlN. Traditionally, aluminum (Al), platinum (Pt), and tungsten (W) have been used as electrode materials. However, the high weight density of Pt and W and the low acoustic impedance of Al are disadvantages for use in high frequency FBAR filters.

Reducing or removing the silicon nitride supporting layer (resistive loss in FIG. 8) by reactive ion etching (RIE) method enhances the sensitivity. Also, performance can be improved by finding the optimum thickness of each electrode material. Having thicker electrode material results in smaller series resistance and reduces resistive losses, but it has higher metal/piezo thickness ratio and acoustic impedance mismatch at the metal/piezo boundary is no longer negligible. Thus, a thinner electrode layer is desired but metal thickness cannot be reduced too much in order to maintain electrical continuity.

Also, noise effects from lateral mode resonance are important to performance. One of the sources of loss in the FBAR is due to the presence of lateral mode resonant frequencies. Spurious mode frequencies can decrease the Q factor because some of the energy is consumed by these spurious modes. Also if the peaks of the spurious modes are high enough to be comparable with the resonant peaks, detecting software (lab view) will give a false resonance value.

One way to suppress the spurious modes is to utilize apodization by using proper electrode shapes. By utilizing a proper shape of the resonator's top electrode, we can avoid edge points of the active area having the same lateral resonant path length. It was found that the square or circle shaped electrodes result in many spurious modes. Experiments using ellipse and pillow shape electrodes shows that the spurious modes are decreased. Additionally, spurious modes can be reduced by adding an additional border in the edge region of the active area. By adjusting overlap area and height between the edge of the parylene diaphragm and the active area, the boundary condition for acoustic displacement will be changed.

The phase noise characteristics of the device can be investigated by using a spectrum analyzer. The resonance frequency of an FBAR is generally found from the phase of the electrical impedance of the device and its change can be detected from the phase change as shown in following equation: $\Delta f = f_0 \Delta \Phi / 2Q$, where $\Delta f$ is a minimum detectable frequency shift, $f_0$ is a resonance frequency, and $\Delta \Phi$ is a minimum detectable minimum phase shift, respectively. However, there are two major limiting factors on the resolution of the minimum phase change detection. One is limited resolution of an evaluation circuit and the other is phase noise of the device itself. Phase noise is spurious noise in the phase plot and evaluated as the maximum deviation from the mean value. The phase noise is inversely proportional to the Q factor. A reduction the Q factor adversely affects the phase noise and the minimum detectable mass. For example, the phase noise of a normal FBAR device increases in water while the Q decreases. Therefore, it is beneficial to characterize and minimize the phase noise characteristics for better resolution of phase change detection.

I claim:

1. A device for sensing a mass in a liquid environment comprising:
    a resonator comprising a piezo layer disposed between a top electrode and a bottom electrode;
    a sensing surface located adjacent the top electrode;
    a gap formed between the top electrode and the sensing surface, the gap structured and operable to provide acoustic energy loss isolation; and
    at least one post disposed between the top electrode and the sensing surface to support the sensing surface and provide the gap.

2. The device of claim 1 wherein the at least one post comprises a plurality of posts.

3. The device of claim 1 wherein the gap is filled with air or a gas.

4. The device of claim 1 wherein the gap is a vacuum gap.

5. The device of claim 1 wherein the resonator is a film bulk acoustic resonator.

6. The device of claim 1 wherein the electrodes are made from a material selected from the group consisting of molybdenum, ruthenium, aluminum (Al), platinum (Pt), and tungsten (W).

7. The device of claim 6 wherein the electrodes are molybdenum or ruthenium.

8. The device of claim 1 wherein the shape of the electrodes are selected from the groups of shapes consisting of a rectangle, a circle, an ellipse and a pillow shape.

9. The device of claim 8 wherein the electrodes are elliptical or pillow shape.

10. The device of claim 1 wherein the sensing surface includes a binding layer for binding a target chemical or biological analyte.

11. The device of claim 1 wherein the gap is sealed by a binding diaphragm.

12. The device of claim 11 wherein the binding diaphragm is made from a low stress silicon nitride.

13. The device of claim 11 wherein the binding diaphragm is between about 0.5 microns and about 1.0 micron thick.

* * * * *